United States Patent [19]

O'Brien et al.

[11] Patent Number: 5,246,854
[45] Date of Patent: Sep. 21, 1993

[54] ATTACHED GROWTH BIOLOGICAL REACTOR

[75] Inventors: Dennis J. O'Brien, Ambler; Wolfgang K. Heiland, Trevose, both of Pa.

[73] Assignee: The United States of America as represented by the Secretary of Agriculture, Washington, D.C.

[21] Appl. No.: 807,334

[22] Filed: Dec. 16, 1991

[51] Int. Cl.$^5$ .................................... C12M 3/04
[52] U.S. Cl. ................................ 435/285; 435/284; 435/310; 435/312; 210/619; 210/150
[58] Field of Search ............... 435/285, 284, 310, 312; 210/619, 150

[56] References Cited

U.S. PATENT DOCUMENTS

| | | | |
|---|---|---|---|
| 2,996,429 | 8/1961 | Toulmin, Jr. | 435/285 |
| 4,004,981 | 1/1977 | Hurni et al. | 435/312 |
| 4,137,172 | 1/1979 | Sako et al. | 210/150 |
| 4,269,719 | 5/1981 | Yamamoto | 210/803 |
| 4,928,623 | 5/1990 | Kojima | 118/249 |
| 4,974,532 | 12/1990 | March | 118/301 |
| 5,003,915 | 4/1991 | D'Amato et al. | 118/46 |
| 5,117,767 | 6/1992 | Sommer | 118/126 |

Primary Examiner—Robert J. Warden
Assistant Examiner—Krisanne M. Thornton
Attorney, Agent, or Firm—M. Howard Silverstein; John D. Fado; Joseph A. Lipovsky

[57] ABSTRACT

An attached growth biological reactor for the growth and harvesting of filamentous fungi. The reactor contains a rigid cylinder which is partially submerged and rotated in a biological medium containing nutrients for fungal growth and which as been inoculated with a filamentous fungal medium. The filamentous fungi attaches itself to and grows upon the cylinder wherein it is removed by use of a doctoring blade. The reactor can be operated in a continuous mode by continuously supplying oxygen and nutrients to the reactor.

10 Claims, 4 Drawing Sheets

ATTACHED GROWTH BIOLOGICAL REACTOR

FIELD OF THE INVENTION

The present invention relates to an attached growth biological reactor designed for the growth and harvesting of filamentous fungi.

BACKGROUND OF THE INVENTION

Much work has been done in recent years on the application of immobilized cell technology for industrial use. This work has focused on the immobilization and growth of bacterial, yeast, and fungal cells. A substantial number of the immobilization methods have been applied to filamentous fungi, some of which have been demonstrated commercially, primarily as substitutes for conventional fermentation systems.

Two of the leading techniques used for immobilization of intact microbial cells are adsorption and entrapment. In adsorption, the cells are linked directly to water-insoluble carriers such as ion-exchanged resins, fritted glass, cordierite, and zirconia ceramic. The adsorption effect is mainly due to electrostatic interactions between the microbial cell surface and the carrier material.

Entrapment involves the use of inert gels, such as polyacrylamide or calcium alginate based gels, wherein the cells become included, or trapped, within the polymeric matrix. The matrix allows diffusion of substrate while preventing cell loss.

While adsorption and entrapment are important for the immobilization of bacteria, yeasts, and some forms of fungi, they may not be necessary, nor may they be the method of choice, for growing and harvesting filamentous fungi. For example, many filamentous fungi will readily form pellets in submerged liquid culture. Because of the physical properties of the aggregated mycelium, fungal pellets can provide a convenient means of immobilizing, or physically confining, the biomass within certain types of reactors, such as column reactors, multi-compartment tank reactors, and tower fermenters.

Filamentous fungi exhibit a strong affinity for surfaces of either organic or inorganic materials and adherence and surface colonization are important features of their natural ecology. Fungal growth on surfaces is sometimes a nuisance and contributes to the difficulty of harvesting such fungi in conventional reactors and fermenters. Although such growth on surfaces is sometimes a nuisance, it can also prove useful. For example, a variety of systems have been developed which, either inadvertently or deliberately, create conditions to promote adherence and surface growth of filamentous fungi. For example, so-called film reactors have been developed wherein a filamentous fungus attaches itself to various structural elements of the reactor.

Also, fixed bed reactors, such as percolating or trickling filters, are used for effluent treatment. In these systems, a microbial population develops as a slime layer on the surfaces of the packing material which is arranged as a fixed bed. Excessive fungal growth is generally considered undesirable and accumulation of a predominantly fungal film causes blockages in the bed with consequent impedance of aeration and drainage.

Several types of rotating biological film reactors, generally referred to as rotating biological contactors (RBC), have been developed for waste water treatment. In these reactors, a microbial film develops on a series of partially submerged discs which rotate slowly in a trough of waste water, thereby exposing the films to both the nutrient water and air. During growth, the film thickens to form a spongy layer which holds an increasing proportion of the medium so that the level in the vessel tends to decrease. This can be a problem in batch operation and the process has to be stopped and the discs sloughed, or scraped, of the microbial buildup.

While much work has been done on methods of growing and harvesting filamentous fungi, there still remains a need in the art for more efficient and effective apparatuses and techniques, particularly those which can be used in a continuous mode.

SUMMARY OF THE INVENTION

In accordance With the present invention, there is provided a biological reactor comprised of:

(a) a horizontally disposed rigid cylinder having an outer surface of sufficient roughness to allow attachment and growth of filamentous fungi, said cylinder being rotatable about its longitudinal axis;

(b) a trough positioned below said cylinder of sufficient length and depth to contain a biological medium in which at least a portion of the cylinder is submerged;

(c) a doctoring blade horizontally disposed and positioned parallel to said cylinder which blade can be brought into contact with the surface of said cylinder to scrape an attached biomass from the surface of said cylinder;

(d) a containing means of sufficient size to receive and contain the biomass scraped from said cylinder; and (e) a rotating means operably attached to said cylinder for rotating the cylinder in the trough; and (f) a vessel having a sealable removable section, which vessel defines a chamber of sufficient size to contain the apparatuses of (a) through (d) above, and which vessel contains: (i) a means for introducing a biological medium directly into said trough; (ii) a means for introducing a sterile oxygen-containing gaseous medium into said chamber; (iii) a means for introducing an inoculum of filamentous fungi onto said cylinder or into said trough, (iv) a port for allowing gases to exhaust from said vessel; (v) a means for allowing the doctoring blade to be operated from outside of said vessel; and (vi) a means for allowing the rotating means, which is positioned outside of said vessel, to be operably connected to the cylinder for causing the cylinder to rotate in the biological medium in the trough.

Also in accordance with the present invention, there is provided a method for growing and collecting a filamentous fungi, which method comprises:

(I) providing a reaction vessel as described immediately supra;

(II) introducing a biological medium into the trough of said reaction vessel which biological medium is one which will support the growth of the filamentous fungus;

(III) introducing an inoculum of filamentous fungus so that it enters the trough;

(IV) rotating the cylinder of said reaction vessel, which is no more than ½ submerged in the medium at an effective rate;

(V) continuously supplying a sterile oxygen-containing gas into the chamber of said reaction vessel;

(VI) applying the doctoring blade to the surface of the cylinder of said reaction vessel when a predetermined amount of mycelia of said fungus has built-up on said cylinder, thereby scraping-off said mycelia; and (VII) collecting the mycelia scraped from the surface of the said cylinder.

DETAILED DESCRIPTION OF THE INVENTION

Figure 1:
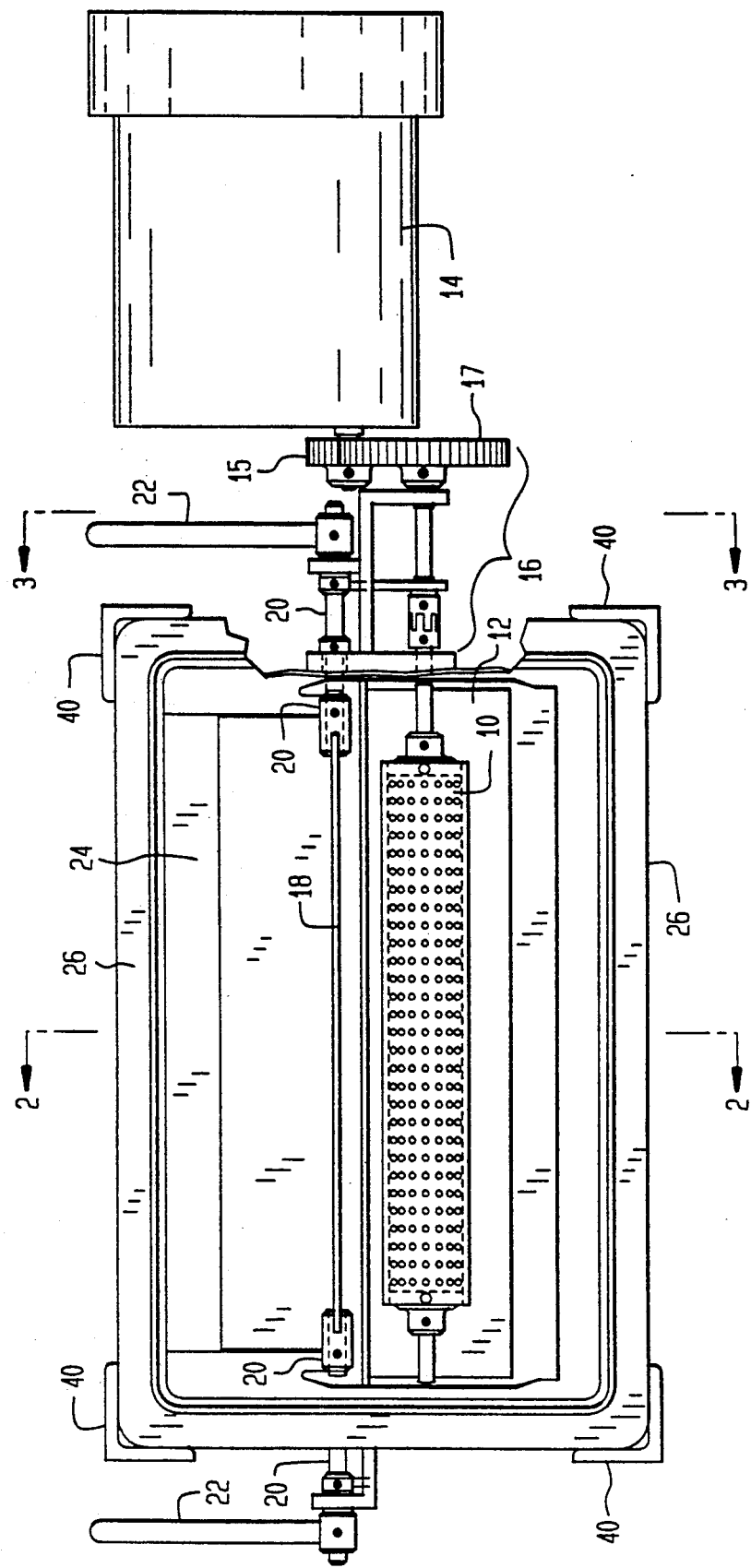
FIG. 1 is a top view of a preferred attached growth biological reactor without the vessel's top in place.

Turning to FIG. 1, there is provided a biological reactor having a cylinder 10 possessing an outer surface which is of sufficient roughness to allow attachment and growth of filamentous fungi. This roughness need not necessarily be severe because many filamentous fungi have a strong affinity for attaching to surfaces. It is preferred, for the practice of the present invention, that the cylinder be a hollow perforated, or grooved, rigid cylinder so that after scraping with the doctoring blade, there will remain a sufficient amount of mycelial growth entrapped on the cylinder for regrowth of the fungus. By "rigid", we mean that the cylinder will not lose its structural integrity under the conditions it is subjected to in the reactor, especially when being scraped by the doctoring blade. Suitable materials from which the cylinder can be manufactured include metals such as stainless steels, as well as polymeric haterials. Suitable polymeric materials include thermosetting resins, preferably polycarbonates. Composite polymer materials may also be used wherein a filler, or fiber component is imbedded in a polymer matrix.

The cylinder is positioned in a trough 12 which is of sufficient length and depth to allow the entire length of the cylinder to be partially submerged in a biological medium which is placed in the trough. The trough, during operation, will contain a biological medium capable of sustaining filamentous fungus growth, or fermentation, or respiration reactions. As the cylinder rotates, it will alternately be in contact with the medium in the trough and the oxygen-containing gaseous environment in the vessel chamber. The depth of the medium in, the trough will be such that no more than half of the cylinder will be submerged in the medium as it rotates. A rotating means 14, for rotating said cylinder, is provided. The preferred rotating means is an electric motor. The rate of rotation of the cylinder should be an effective rate. That is, one which will not be so slow that the growing biomass will be deprived of oxygen or so fast as to disrupt its growth. Suitable speeds will typically be from about 2 to about 10 rpm, preferably about 4 to about 7 rpm. Any suitable collective mechanism means, such as an assortment of gears, shafts, couplings, etc., designated collectively herein as 16 and having a gear 17, can be provided to suitably connect, or mesh, with the motor mechanism, such as gear 15. Such suitable means are well known to those skilled in the art.

A doctoring blade 18 is provided which is operably connected to a pivoting means 20 containing handles 22 as a positioning means for pivoting the doctoring blade away from, or onto, the cylinder surface on which the mycelia biomass is growing. While this figure shows the blade being operated by use of a handle and pivoting means, it is understood that any suitable positioning means, or mechanism, can be used. For example, it is within the scope of the present invention that the blade be operated by an electro-mechanical mechanism, which can be electrically started from outside of the vessel. The electro-mechanical mechanism can also be automated so that when the fungal layer builds to a predetermined thickness on the cylinder, a signal is sent to the electro-mechanical mechanism to initiate the operation of the doctoring blade. When in contact with the surface of the cylinder, the blade scrapes the biomass off of the cylinder wherein it slides into containing means 24. It will be noted that the reactor of the present invention is designed so that the positioning means of the pivoting means is located outside of the vessel, which is discussed below. Thus, there needs to be an operable seal, otherwise known as a dynamic seal, at the wall of the vessel connecting the internal mechanism with the external mechanism of the positioning means.

The entire apparatus of cylinder, trough, doctoring blade, and containing means, is located within a substantially airtight vessel 26 of sufficient size to contain said apparatus. The vessel is fabricated from a material, preferably a metal such as a stainless steel, which will allow the vessel and its contents to be sterilized at conventional autoclave conditions. Typical autoclave conditions would include a temperature of about 120° C. at about 15 psi for about 20 minutes. The vessel is preferably comprised of two sealable and detachable parts to allow the entry and exit of any one or more components of the previously described apparatus. Also shown in FIG. 1 is a securing means 40 for fixably locating the vessel for positioning and stability purposes. Precise positioning is needed for aligning the gear 17 of collective mechanism 16 with gear 15 of rotating means 14, which is preferably an electrical motor. The securing means itself can be secured to a table, bench etc.

Figure 2:
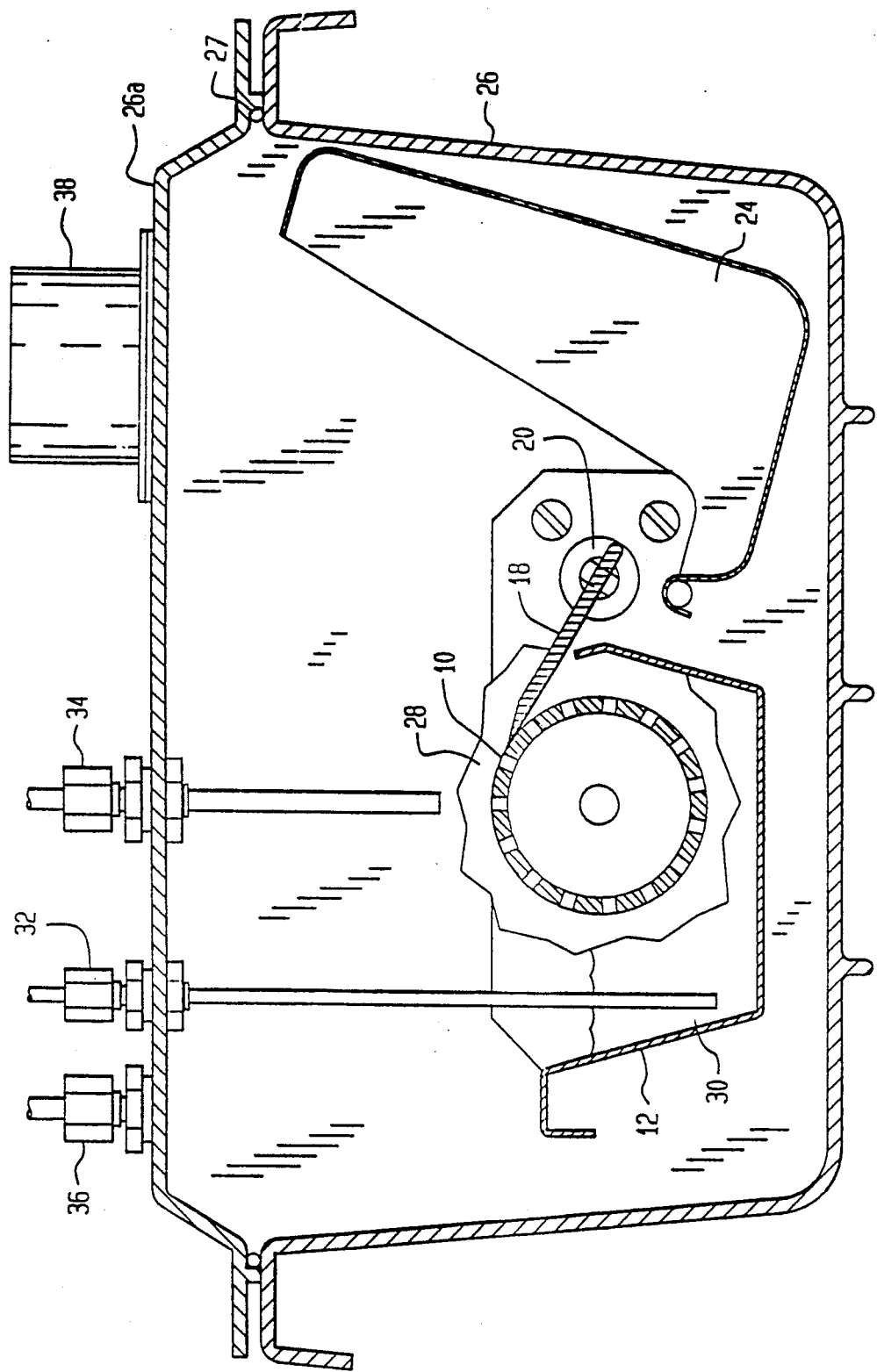
FIG. 2 is an end view of the same reactor but along plane 2—2, but with the vessel's top in place.

Turning now to FIG. 2, there is shown a side view along plane 2—2 of FIG. 1. Cylinder 10 is shown having a mycelia biomass 28 attached thereto, which cylinder is partially submerged within the biological medium 30 in trough 12. The medium can be any appropriate medium which will support the growth of filamentous fungi. Growth mediums for filamentous fungi are well known in the art and typically include a carbon source, such as glucose, dextrose, or corn starch; a nitrogen source, such as yeast extract, an optional phosphorus source; and other nutrients as required. A preferred medium will contain a lactose substance as the carbon source for the production of 5,8,11,14,17 - eicosapentaenoic acid, which can be produced by some filamentous fungi. A preferred lactose substance is whey, more preferably sweet whey permeate, a by-product of cheese production and which typically contains about 5 wt. % lactose. Spray-dried sweet whey permeate will typically contain about 80 wt. % lactose.

Doctoring blade 18 is shown in contact with the surface of the cylinder. The blade has been put into contact by pivoting means 20. Once in contact with the surface of the cylinder, the blade scrapes the surface of the cylinder and lifts the attached biomass therefrom so that as the cylinder rotates, the biomass slides down the blade and into containing means 24. It is preferred that the containing means, which can simply be a holding tray, be removable from the other pieces of apparatus so that the collected biomass can easily be removed from the vessel for subsequent use or processing.

Figure 3:
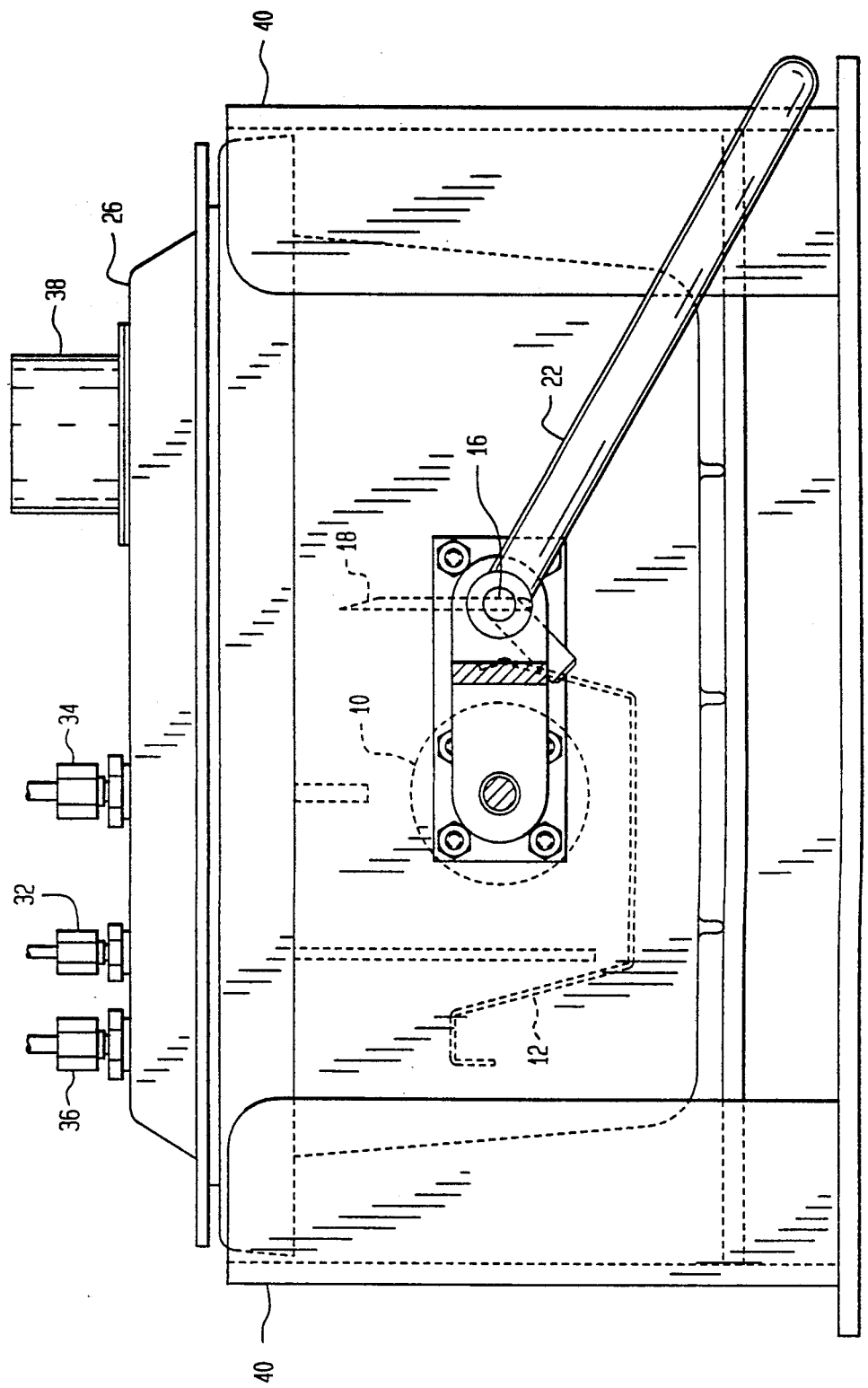
FIG. 3 is another end view of the same reactor but along plane 3—3.

The vessel is shown with a sealable detachable top section 26a which, when connected to the bottom section of the vessel, creates a substantially airtight seal. Any suitable means can be used to create the air tight seal, for example, an elastomeric o-ring as shown in the figure as 27, can be used. The top of the vessel contains a means 32 for delivering a biological medium directly into the trough 12 without the need for removing the vessel top. This allows the medium to be delivered into the trough under sterile conditions. An inoculum of filamentous fungus can be deposited directly onto the cylinder by means 34. It will be understood that the inoculum can also be introduced directly into the trough. There is also provided a means 36 for delivering a sterile oxygen-containing gas, preferably air, into the vessel. It is preferred that the gas be passed through a sterilizing filter prior to its entry into the chamber. The air can be provided to the vessel by a pump of suitable capacity. While any appropriate means can be used for introducing the oxygen-containing gas, inoculum, and medium into the reactor, preferred means are shown in FIGS. 2 and 3. These preferred means are comprised of tubing of suitable diameter, preferably stainless steel tubing, secured to the vessel via suitable sealable bulkhead fittings. There is also provided an exhaust port 38 which is preferably stuffed with a porous or fibrous, material such as cotton or glass wool to help prevent entry of microorganisms.

FIG. 3 hereof is another side view of the preferred biological reactor of FIG. 1, except it is shown along plane 3—3. Handle 22 of the previously described pivoting means 20 is shown outside of vessel 26. The handle is connected to shaft 16 which is part of said pivoting means and which extends through the wall of the vessel by a dynamic seal which operably connects the outside mechanism with the inside mechanism in a substantially airtight manner. By moving the handle, the doctoring blade 18 can be brought into contact with the surface of cylinder 10 to scrape and remove any attached biomass therefrom. Other numbered parts shown in this FIG. 3 have already been described in the discussion with respect to FIG. 2.

The biological reactor of the present invention can be operated to produce filamentous fungi by first preparing an inoculum of filamentous fungus, such as Saoroleonia oarasitica. If it is desired to produce 5,8,11,14,17 - eicosabentaenoic acid (EPA), then an EPA producing filamentous fungus must be used. Preferred are those which can also utilize lactose as a substrate for growth. Non-limiting examples of such fungi include those from the class known as Oomycetes, preferably *Pythium ultimum* (ATCC 11123), *Pythium debaryanum* (ATCC 9998), *Pythium sp*(ATCC 11270) and *Pythium irregulare* (ATCC 10951). More preferred is *Pythium irregulare*. The inoculum can be prepared by incubating the filamentous fungus, or mycelium, obtained from a growing medium on an agar slant in a suitable medium at an effective temperature, preferably a temperature from about 20° to about 25° C., for an effective period of time for incubation to occur. The period of time will generally be a few days. After incubation, the resulting mycelial clump can be macerated in a glucose-free media, preferably in a blender. Prior to introducing the inoculum into the reactor, the reactor, a glucose-free medium, and a glucose solution are sterilized. For example, each one is separately sterilized in an autoclave under appropriate conditions for an effective period of time to obtain substantial sterilization. Upon cooling, the glucose-free medium, the glucose solution, and the inoculum are introduced into the reactor, which has also been sterilized, to initiate the growth of the filamentous fungus. The entire reactor and contents can be put in an incubator at an appropriate temperature, preferably at a temperature from about 20 to about 25° C. A sterile oxygen-containing gas is continuously introduced into the reactor during growth of the mycelia. Also, the medium can be continuously introduced if it is desired to run the reactor in a continuous mode.

After the mycelia has sufficiently covered the rotating cylinder, the doctoring blade is applied and the cylinder is scraped of the biomass. The run can be continued to allow the mycelia to regrow on the cylinder. Additional nutrients are added at approximately the rate at which they are consumed.

Having thus described the invention, the following example is presented for illustrative purposes only and should not be taken as limiting the invention in any way.

EXAMPLE

A medium having the following composition was prepared:

| | |
|---|---|
| $KH_2PO_4$ | 1.361 g/l |
| EDTA | 0.50 |
| $MgCl_2.6H_2O$ | 0.50 |
| $MnCl_2.4H_2O$ | 0.1435 |
| $ZnCl_2$ | 0.0835 |
| $CaCl_2.2H_2O$ | 0.0366 |
| $FeCl_3.6H_2O$ | 0.0048 |
| DL-Methionine | 0.05 |
| L-Sodium Glutamate | 2.00 |
| Yeast Extract | 1.00 |
| Biotin | 0.10 |
| Glucose | 5.00 |

An inoculum of the filamentous fungus, *Saproleonia parasitica*, was prepared by incubating mycelia obtained from a growing medium on a agar slant in 110 ml of medium at about 24° C. for three days. After incubation, the mycelial clump was transferred to a Waring-type blender and macerated in a glucose-free media. The resulting mixture was introduced into the reactor represented by FIGS. 1 to 3 hereof.

Prior to running the experiment, the reactor, the glucose-free medium, and a 56 g/l glucose solution were autoclaved separately at 120° C., 15 psi, for 20 minutes. Upon cooling, the glucose-free medium, the glucose solution, and the inoculum were introduced into the reactor to initiate the experiment. The reactor was placed inside an incubator at about 24° C.

Glucose concentrations were monitored throughout the experiment and were converted to estimated dry weight of mycelia with the use of the yield coefficient (gm dry weight/gm glucose consumed) calculated after the conclusion of the experiment from the final dry weight. During the experiment, the glucose concentration was maintained at or close to 3 g/l. The pH was maintained, at or close to, 7.

After the mycelia had sufficiently covered the rotating cylinder (approximately 40 hours), the doctoring blade was applied to scrape the cylinder surface of mycelia. The mycelia was collected in the containing means. The experiment was continued to allow the mycelia to regrow over the cylinder.

Figure 4:
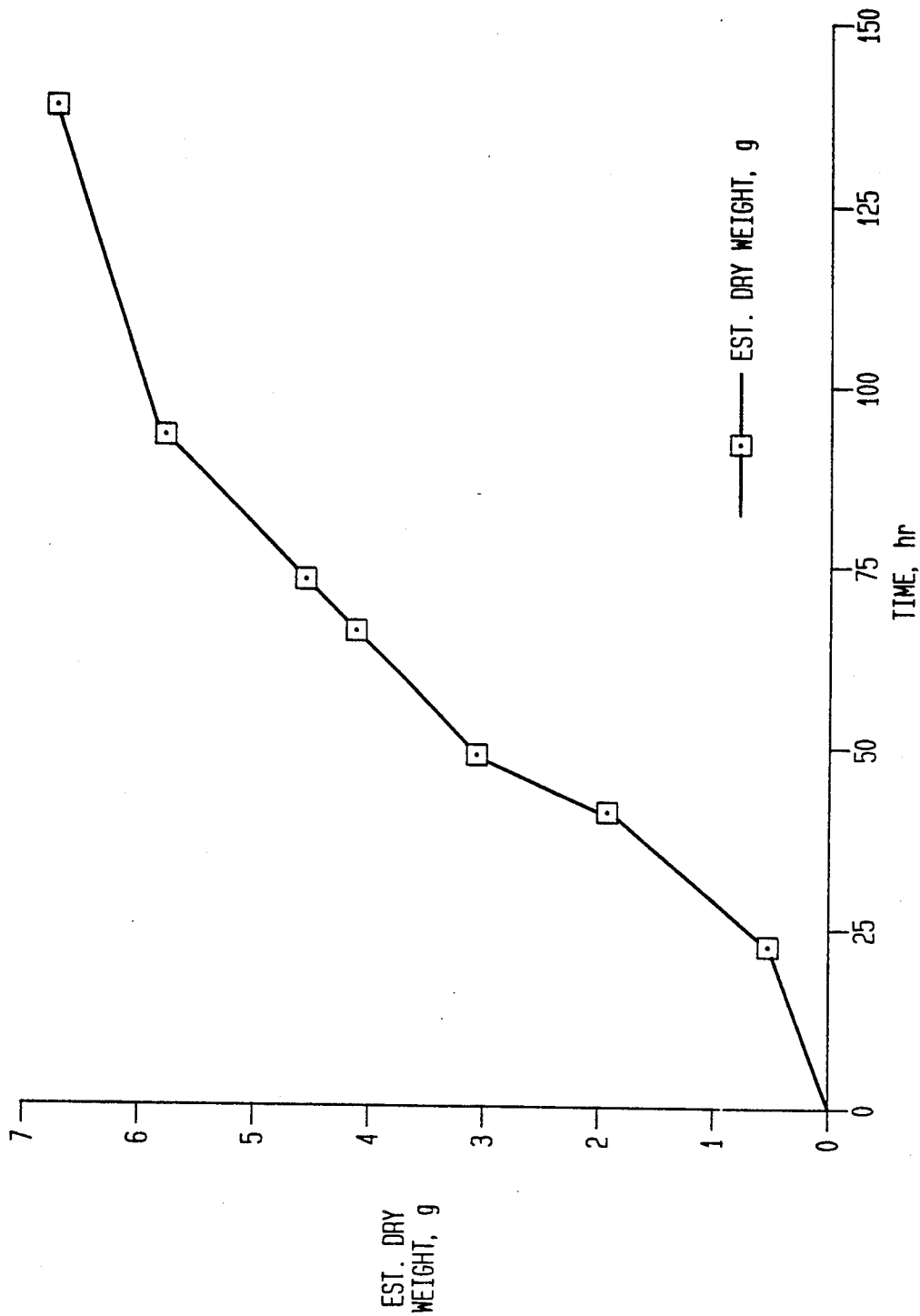
FIG. 4 is a graphical representation of the results obtained by the example hereof showing total estimated dry weight of collected mycelia versus time.

A plot of the estimated total dry weight mycelia vs time is shown in FIG. 4 hereof.

What is claimed is:

1. A biological reactor comprised of:
   (a) a horizontally disposed rigid cylinder having an outer surface of sufficient roughness to allow attachment and growth of filamentous fungi, said cylinder being rotatable about its longitudinal axis;
   (b) a trough positioned below said cylinder of containing a biological medium in which at least a portion of the cylinder is submerged;
   (c) a doctoring blade horizontally disposed and positioned parallel to said cylinder which blade can be brought into contact with the surface of said cylinder to scrape an attached biomass from the surface of said cylinder;
   (d) a container of sufficient size to receive and contain the biomass scraped from said cylinder which is located proximate to said doctoring blade such that material scraped from the surface of said cylinder by said blade is deposited by gravity into said container; and
   (e) a rotating means operably attached to said cylinder for rotating the cylinder in the trough; and
   (f) a vessel having a sealable removable section, which vessel defines a chamber containing the apparatuses of (a) through (d) above, and which vessel further contains:
       (i) a means for introducing a biological medium into said trough; (ii) a means for introducing a sterile oxygen-containing gaseous medium into said chamber; (iii) a means for introducing an inoculum of filamentous fungi onto said cylinder or into said trough, (iv) a port for allowing gases to exhaust from said vessel; (v) a means for allowing the doctoring blade to be positioned from outside of said vessel; and (vi) a means for allowing the rotating means, which is positioned outside of said vessel, to be operably connected to the cylinder for causing the cylinder to rotate in the biological medium in the trough.

2. The reactor of claim 1 wherein the cylinder is comprised of a thermosetting polymeric material.

3. The reactor of claim 2 wherein the thermosetting material is a polycarbonate.

4. The reactor of claim 1 wherein the doctoring blade is positioned by a pivoting means which is operable from outside of said vessel.

5. The reactor of claim 2 wherein the doctoring blade is positioned by use of a pivoting means which is operable from outside of the vessel.

6. A method for growing and collecting a filamentous fungi, which method comprises:
   (I) providing a biological reactor according to claim 1:
   (II) introducing a biological medium into the trough which biological medium is one which will support the growth of the filamentous fungus;
   (III) introducing an inoculum of filamentous fungus so that it enters the trough;
   (IV) rotating the cylinder, which is no more than ½ submerged in the medium at a rate effective to avoid oxygen deprivation or growth disruption of the filamentous fungus attached thereto;
   (V) continuously supplying a sterile oxygen-containing gas into said chamber;
   (VI) applying the doctoring blade to the surface of the cylinder when a predetermined amount of mycelia of said fungus has built-up on said cylinder, thereby scraping-off said mycelia; and
   (VII) collecting the mycelia scraped from the surface of the said cylinder.

7. The method of claim 6 wherein the cylinder is comprised of a polycarbonate material.

8. The method of claim 6 wherein the doctoring blade is positioned by a pivoting means which is operable from outside of said vessel.

9. The method of claim 6 wherein the oxygen-containing gas is air.

10. The method of claim 6 wherein the cylinder is comprised of a thermal setting polymeric material; the doctoring blade is positioned by use of a pivoting means which is operable from outside of the vessel; and the oxygen-containing gas is air.

* * * * *